United States Patent [19]
Hubbell et al.

[11] Patent Number: 5,644,947
[45] Date of Patent: Jul. 8, 1997

[54] TENSIOMETER AND METHOD OF DETERMINING SOIL MOISTURE POTENTIAL IN BELOW-GRADE EARTHEN SOIL

[75] Inventors: Joel M. Hubbell; James B. Sisson, both of Idaho Falls, Id.

[73] Assignee: Lockheed Idaho Technologies Company, Idaho Falls, Id.

[21] Appl. No.: 376,165

[22] Filed: Jan. 19, 1995

[51] Int. Cl.$^6$ .................................................... G01N 7/10
[52] U.S. Cl. .................................... 73/73; 73/152.54
[58] Field of Search ............................. 73/73, 152.01, 73/152.54

[56] References Cited

U.S. PATENT DOCUMENTS

| | | | |
|---|---|---|---|
| 2,878,671 | 3/1959 | Prosser et al. | 73/73 |
| 3,043,133 | 7/1962 | Richards | 73/73 |
| 3,049,914 | 8/1962 | Richards | 73/73 |
| 3,871,211 | 3/1975 | Tai | 73/73 |
| 3,898,872 | 8/1975 | Skaling et al. | 73/73 |
| 4,068,525 | 1/1978 | Skaling . | |
| 4,520,657 | 6/1985 | Marthaler | 73/73 |

FOREIGN PATENT DOCUMENTS

| | | | |
|---|---|---|---|
| 1174635 | 12/1969 | United Kingdom | 73/73 |
| 1454674 | 11/1976 | United Kingdom | 73/73 |

OTHER PUBLICATIONS

James, M. L., et al., *Applied Numerical Methods for Digital Computation*, (3rd), Harper & Row, NY, pp. 86–93.

Primary Examiner—William A. Cuchlinski, Jr.
Assistant Examiner—Willie Morris Worth
Attorney, Agent, or Firm—Wells St. John Roberts Gregory & Matkin

[57] ABSTRACT

A portable tensiometer to in situ determine below-grade soil moisture potential of earthen soil includes, a) a body having opposing first and second ends and being adapted for complete insertion into earthen soil below grade; b) a porous material provided at the first body end, the porous material at least in part defining a fluid chamber within the body at the first body end, the fluid chamber being fluidically sealed within the body but for the porous material; c) a degassed liquid received within the fluid chamber; d) a pressure transducer mounted in fluid communication with the fluid chamber; e) the body, pressure transducer and degassed liquid having a combined mass; f) a flexible suspension line connected to the body adjacent the second body end, the flexible line being of sufficient strength to gravitationally freely self suspend the combined mass; and c) the combined mass being sufficient to effectively impart hydraulic communication between below-grade earthen soil contacted by the porous material under the weight of the combined mass. Tensiometers configured to engage the sidewalls of an earthen opening are also disclosed. Methods of taking tensiometric measurements are also disclosed.

4 Claims, 6 Drawing Sheets

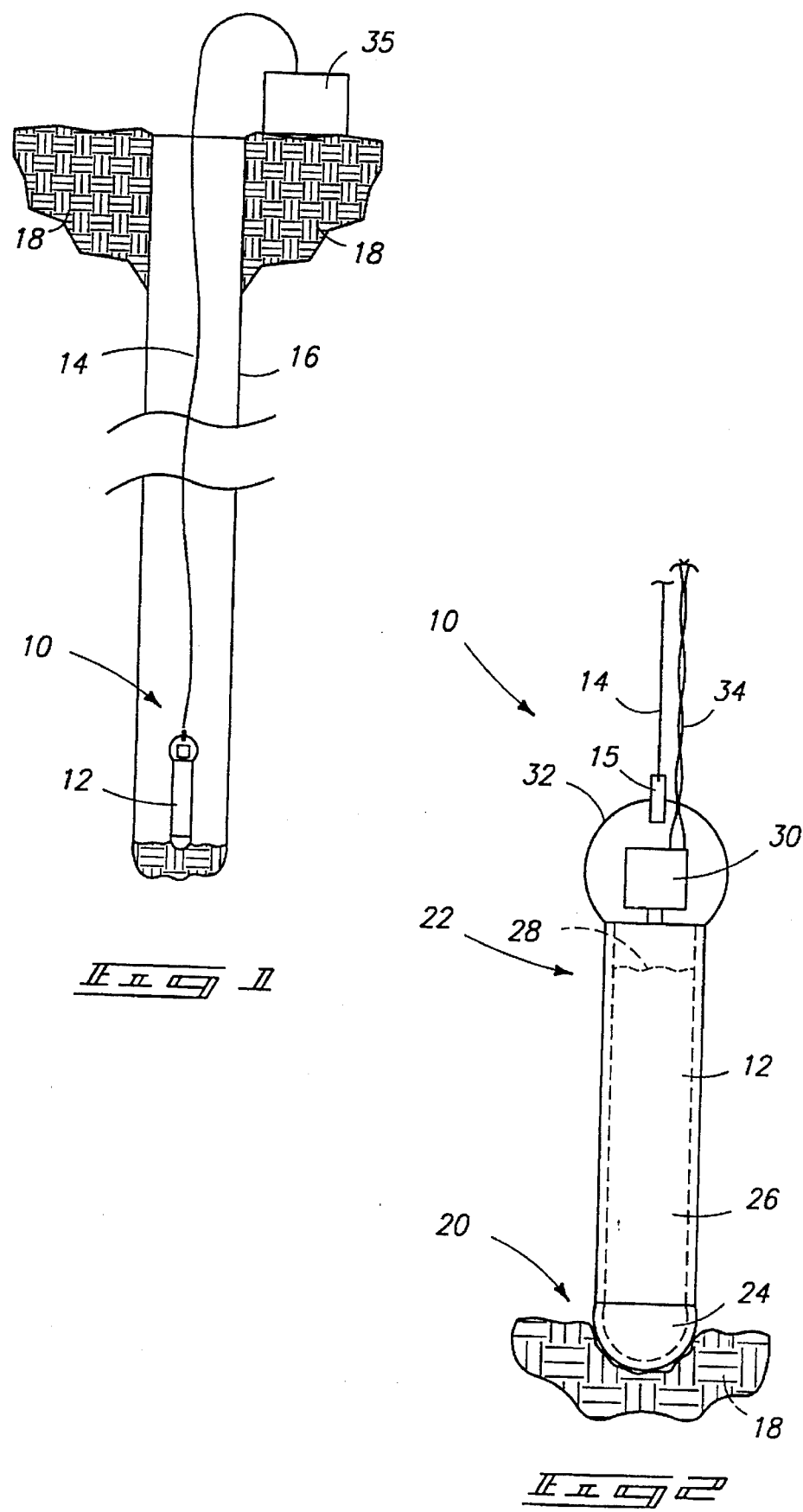

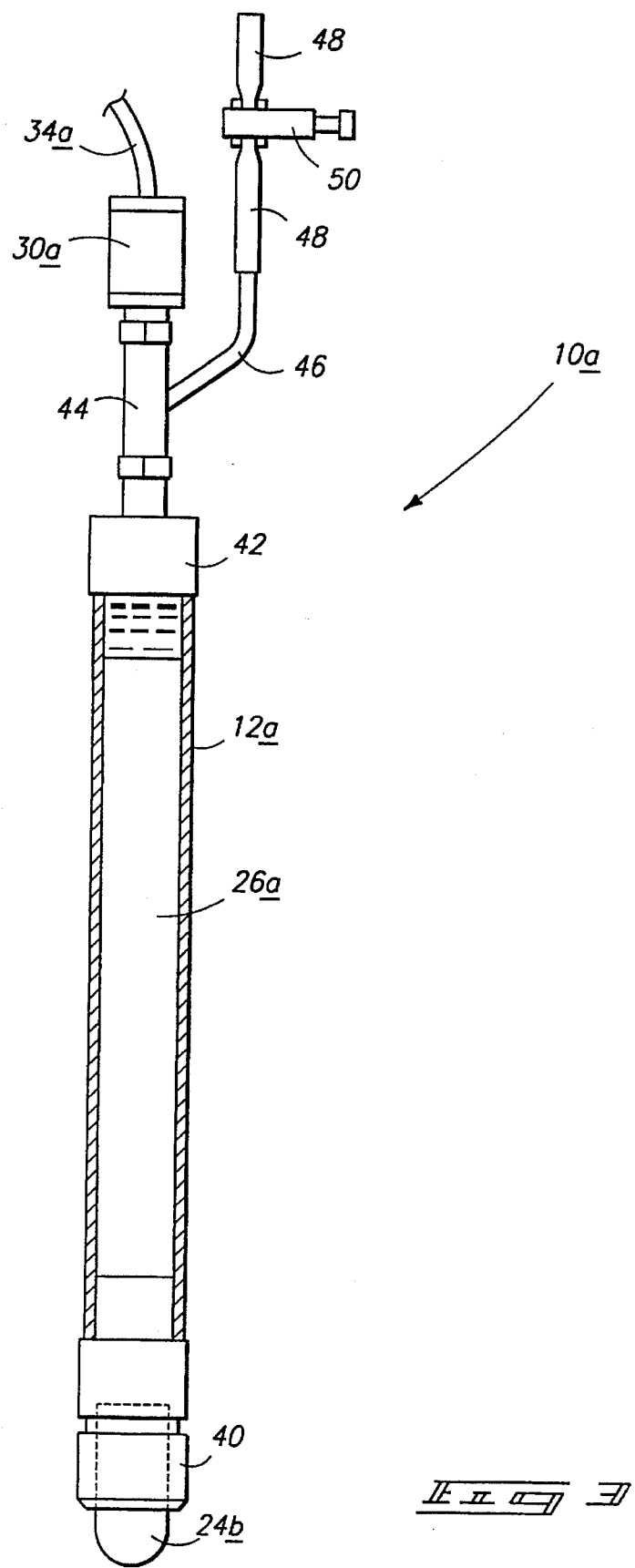

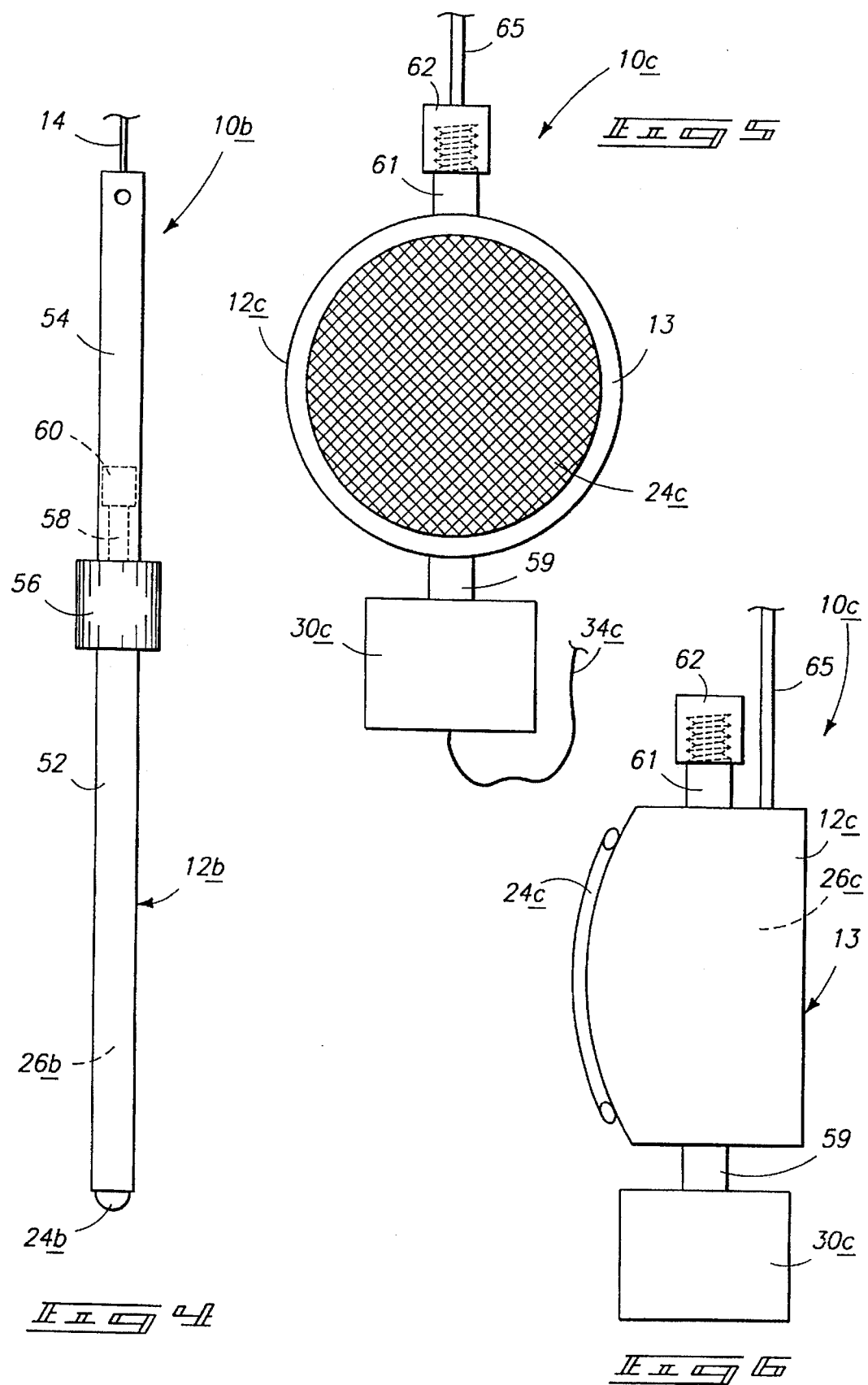

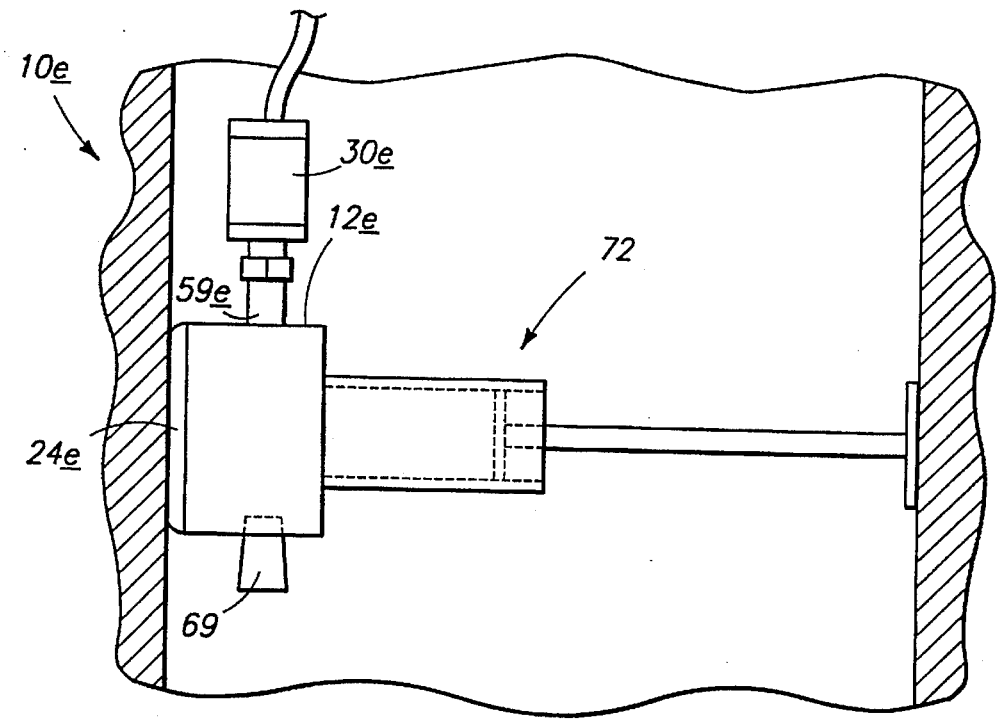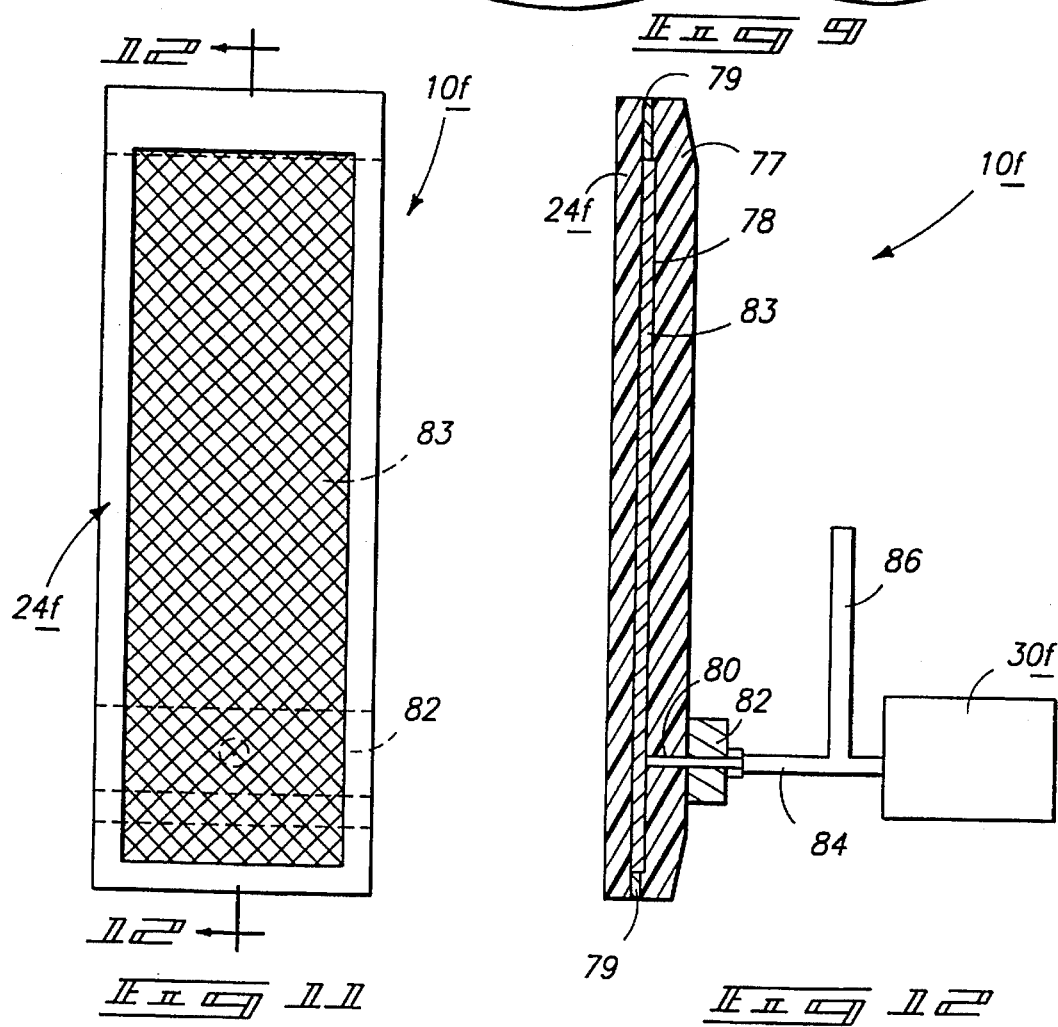

5,644,947

TENSIOMETER AND METHOD OF DETERMINING SOIL MOISTURE POTENTIAL IN BELOW-GRADE EARTHEN SOIL

CONTRACTUAL ORIGIN OF THE INVENTION

The U.S. Government has rights in this invention disclosed under contract number DE-AC07-76ID01570 between the U.S. Department of Energy and EG&G Idaho, Inc., now contract number DE-AC07-94ID13223 with Lockheed Idaho Technologies Company.

TECHNICAL FIELD

This invention relates to tensiometers and to techniques for measuring soil moisture potential using tensiometers.

BACKGROUND OF THE INVENTION

If moisture potential of soil can be accurately monitored, irrigation can be controlled to optimize the rate of plant growth. One type of instrument for measuring soil moisture potential is a tensiometer. A conventional tensiometer comprises a sealed tube defining a chamber which is normally completely filled with water, a hollow porous tip on one end of the tube, and a vacuum gauge connected to the water chamber. The porous tip is inserted in the soil, and establishes liquid contact between the water in the tube and moisture in the soil surrounding the tip. Relatively dry soil tends to pull water from the tube through the porous tip. However since the tube is sealed, only a minute amount of water is actually withdrawn. Accordingly, the water in the tube is placed under tension by the pulling effect of the dry soil, thus creating a measurable subatmospheric pressure in the tube. Higher moisture contents in the soil produce correspondingly less vacuum in the tube, and completely saturated soil registers substantially zero vacuum or atmospheric pressure.

Typical tensiometer constructions provide a tube or column of water which extends from the porous tip to above grade. It will be apparent that the deeper the porous tip is buried, the longer the column of liquid above it will become.

Air presence in the water reservoir during tensiometric measurement is undesirable. Air can enter the reservoir by diffusing through the porous tip. More commonly, dissolved air present in the water that enters the vessel comes out of solution in the reduced pressure environment of the tensiometer. Eventually, the entire tensiometer would become filled with air. This air will increase the time required to reach pressure equilibrium because large volumes of water must move through the porous tip to effect the mass transfer of air through the tip. Thus in order to obtain accurate readings, the water and air are desirably purged periodically from the tensiometer reservoir and replaced with degassed water.

To facilitate purging of air from the tensiometer reservoir, a conventional tensiometer is typically provided with a column of water connecting a surface located pressure measuring device to the soil-embedded porous tip. However, there is a physical limit to the length of a column of water which can be supported by atmospheric pressure (about 1000 cm at sea level), and the useful measurement range of the tensiometer is reduced as the column of water above the porous tip is lengthened. The pressure exerted by the column of water increases the pressure in the porous tip, which in turn increases the apparent soil moisture tension recorded by the above-surface pressure measuring device.

BRIEF DESCRIPTION OF THE DRAWINGS

Preferred embodiments of the invention are described below with reference to the following accompanying drawings.

FIG. 1 is a diagrammatic representation of a portable tensiometer apparatus positioned within a borehole for measurement in accordance with the invention.

FIG. 2 is an enlarged view of a portion of FIG. 1.

FIG. 3 is a side sectional view of a reduction-to-practice embodiment of a tensiometer in accordance with the invention.

FIG. 4 is a diagrammatic elevational view of an alternate reduction-to-practice embodiment of a portable tensiometer in accordance with the invention.

FIG. 5 is a diagrammatic side elevational view of still another reduction-to-practice tensiometer in accordance with the invention.

FIG. 6 is a side elevational view corresponding to that of FIG. 5, but for a 90° rotation of the tensiometer.

FIG. 9 is a longitudinal sectional view of an alternate embodiment sidewall tensiometer apparatus in accordance with the invention.

FIG. 11 is a diagrammatic side elevational view of another alternate embodiment sidewall tensiometer apparatus in accordance with the invention.

FIG. 12 is a side sectional view the FIG. 11 tensiometer apparatus.

DETAILED DESCRIPTION OF THE PREFERRED EMBODIMENTS

Figure 7:
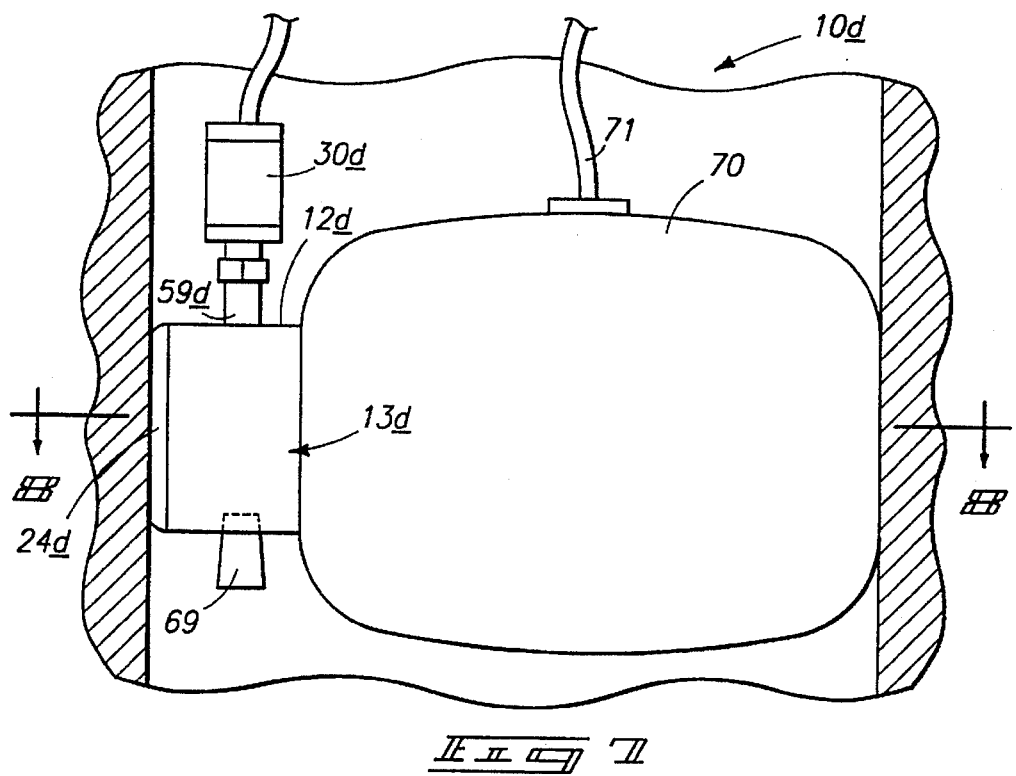
FIG. 7 is a longitudinal sectional view of a sidewall tensiometer device in accordance with the invention as positioned within a borehole for tensiometric measurement.

This disclosure of the invention is submitted in furtherance of the constitutional purposes of the U.S. Patent Laws "to promote the progress of science and useful arts" (Article 1, Section 8).

In accordance with one aspect of the invention, a portable tensiometer to in situ determine below-grade soil moisture potential of earthen soil comprises:

a body having opposing first and second ends and being adapted for complete insertion into earthen soil below grade;

a porous material provided at the first body end, the porous material at least in part defining a fluid chamber within the body at the first body end, the fluid chamber being fluidically sealed within the body but for the porous material;

a degassed liquid received within the fluid chamber;

a pressure transducer mounted in fluid communication with the fluid chamber;

the body, pressure transducer and degassed liquid having a combined mass;

a flexible suspension line connected to the body adjacent the second body end, the flexible line being of sufficient strength to gravitationally freely self suspend the combined mass; and the combined mass being sufficient to effectively impart hydraulic communication between below-grade earthen soil contacted by the porous material under the weight of the combined mass.

In accordance with another aspect of the invention, a method of monitoring soil moisture potential in below-grade earthen soil comprises the following steps:

providing a body having opposing first and second ends, a porous material provided at the first body end, the porous material at least in part defining a fluid chamber within the body at the first end, the fluid chamber being fluidically sealed within the body but for the porous material, a degassed liquid received within the fluid chamber, a pressure transducer mounted in fluid communication with the fluid chamber;

lowering the body, transducer and degassed liquid below grade into an opening provided in earthen soil using a flexible line attached to the body adjacent the second body end;

continuing to lower the body, transducer and degassed liquid within the earth opening until the porous material reaches and contacts a lowestmost base terminus of the earth opening;

slackening the flexible line to self support the body, transducer, and degassed liquid against the earthen opening base through the porous material under their own combined weight, the weight being sufficient to establish effective hydraulic communication between the earthen soil and the porous material;

permitting the degassed liquid to permeate the porous material to cause a change in pressure in the fluid chamber; and determining the change in pressure with the pressure transducer.

In accordance with still a further aspect of the invention, a portable tensiometer to in situ determine below-grade soil moisture potential of earthen soil comprises:

a body having opposing first and second ends and being adapted for complete insertion into earthen soil below grade;

a porous material provided at the first body end, the porous material at least in part defining a fluid chamber within the body at the first body end, the fluid chamber being fluidically sealed within the body but for the porous material;

a degassed liquid received within the fluid chamber;

the body and degassed liquid having a combined mass;

a flexible suspension line connected to the body adjacent the second body end, the flexible line being of sufficient strength to gravitationally freely self suspend the combined mass; and the combined mass being sufficient to effectively impart hydraulic communication between below-grade earthen soil contacted by the porous material under the weight of the combined mass.

In accordance with still yet a further aspect of the invention, a tensiometer to in situ determine below-grade soil moisture potential of earthen soil comprises:

a body adapted for insertion into an opening in earthen soil below grade, the body having lateral sidewalls;

a laterally oriented porous material provided relative to the body lateral sidewalls, the laterally oriented porous material at least in part defining a fluid chamber within the body;

a pressure sensor in fluid communication with the fluid chamber; and sidewall engaging means for engaging a portion of a sidewall of an earth opening to laterally urge the porous material into hydraulic communication with earthen soil of another portion of the opening sidewall.

In accordance with still yet another aspect of the invention, a method of monitoring soil moisture potential in below-grade earthen soil comprises the following steps:

inserting a tensiometer into an earthen opening below grade in earthen soil; the tensiometer having a porous material, a fluid chamber in fluid communication with the porous material, and a degassed liquid within the fluid chamber laterally urging the porous material against a sidewall of the earthen opening to effectively establish hydraulic communication between the fluid chamber and the earthen material;

permitting the degassed liquid to permeate the porous material to cause a change in pressure in the fluid chamber; and determining the change in pressure within the chamber.

More particularly and first with reference to FIGS. 1 and 2, a portable tensiometer is indicated generally with reference numeral 10. Tensiometer apparatus 10 comprises a body 12 and flexible suspension line 14. Line 14 is utilized to raise and lower body 12 relative to a bore 16 provided within earthen soil 18. The artisan will recognize utility of the devices and methods disclosed herein with other earthen openings, such as trenches and exposed earthen faces.

Body 12 has opposing first and second ends 20 and 22, respectively. Body 12 is adapted or configured for complete insertion into earthen soil entirely below grade. Body or housing 12 is substantially cylindrically hollow, having a conventional ceramic or other material porous tip 24 provided at its first end 20. Porous material or tip 24 in part defines a fluid chamber 26 within body 12 at first body end 20. Fluid chamber 26 is fluidically sealed within body 12 but for pores provided in porous material 24. Degassed liquid 28, typically degassed water, is received within fluid chamber 26. A pressure transducer 30 is mounted in fluid communication with fluid chamber 26 at first body end 22. Transducer 30 is shown as being mounted externally relative to body 12, although internal sealed mounting would of course also be contemplated. A ring hanger 32 is received at second body end 22, and joins with flexible suspension line 14 via a suitable connector 15. Wires 34 connect with transducer 30 and extend outwardly of pressure transducer 30 along flexible line 14 to the surface. Such are not shown in FIG. 1 for clarity. Wires 34 would extend to a data logger 35 above ground, such as the 21× Micro Logger, available from Campbell Scientific, Inc., of Logan, Utah.

Elongated body 12 and its associated components, such as pressure transducer 30 and ring hanger 32, in combination with a quantity of degassed liquid 28 therewith, have a combined mass which is sufficient to effectively impart hydraulic communication between the below grade earthen soil 18 contacted by porous material 24 under the weight of the combined mass. The apparatus would be utilized in accordance with an aspect of the invention by lowering the illustrated components with flexible line 14 into bore 16 below grade. The illustrated components would continue to be lowered within bore 16 until porous material 24 reaches and contacts a lowestmost base terminus of bore 16, as shown in FIGS. 1 and 2. Flexible line 14 would thereafter be slackened, as shown in FIG. 1, to cause body 12 and its associated components and contents to be self-supported against the bore base under its own combined weight, with that weight being gauged to be sufficient to establish effective hydraulic communication between the earthen soil and the porous material.

Prior art tensiometers have heretofore utilized rigid interconnection to the surface enabling the porous material of the tensiometer to extend downwardly into the base of the bore to provide suitable hydraulic communication with the soil. However, care in the prior art must have been taken to assure that the porous tip was not overly compressed into the bore base, as such could cause temporary inaccurate tensiometric measurements due to soil compaction at best, or destruction of the porous tip at worst. In accordance with the invention, intervening hydraulic facilitating material (fine grained silica flour or other suitable fine grained material) might be placed within the base of bore 16 prior to insertion of tensiometer apparatus 10 therewithin.

A reduction-to-example tensiometer apparatus 10a is described with reference to FIG. 3. Like numerals from the FIGS. 1–2 embodiment are utilized where appropriate, with differences being indicated by addition of the suffix "a". Tensiometer apparatus 10a has a housing 12a comprised of a 12-inch length of clear EDPM tubing. A one-bar, high-flow porous ceramic cup 24b of approximately 2½ inches in length and ⅞ inch in diameter is attached to tubing 12a with a compression fitting 40 and an O-ring (not shown). The compression fitting is cemented to tubing 12a utilizing conventional epoxy or PVC cement. The upper portion of tubing 12a is provided with a PVC mating connector 42 having ¾-inch female threads provided therein. A ¾-inch diameter, 2-inch long metal coupler 44 connects tubular body 12a with a pressure transducer 30a. An example transducer is Model ST2P15G1, having a range of from −15 to −15 psig, sold by SenSym of Milpitas, Calif. Wires 34a extend outwardly of transducer 30a to an above ground data logger.

Coupler 44 is provided with a ½-inch tube 46 welded into its center that extends outward and upward in the same general direction as transducer 30a, yet initially at an angle therefrom. Tubing 46 connects with access tubing 48, which is provided with a pinch clamp 50 or similar device, for filling and sealing fluid chamber 26a within housing 12a.

Tensiometer apparatus 10a is prepared for use by first filling it with degassed liquid, such as degassed water. To do so, valve 50 is opened and degassed water is placed into chamber 26a through tubing 48 and 46. This is most preferably conducted by inserting the nozzle of a squeeze bottle (not shown), containing degassed water, into the open end of upper tube 48. The squeeze bottle nozzle is sufficiently small to enable air to escape therearound from chamber 26a when the apparatus is filled. When chamber 26a has been completely filled with de-aired water and all air removed, valve 50 is closed so as to seal chamber 26a from the atmosphere. Tensiometer apparatus 10a is installed by lowering it, for example, by means of electrical wires 34 or a separately attached rope, wire or cord, into a borehole completed to the depth of interest until porous cup 24b makes hydraulic contact with indigenous material or sediment at the bottom of the hole.

Slackening of the flexible line lets the entire mass of the housing and its associated components rest in hydraulic communication with the sediment. For example, the above-described components, when completely filled with degassed water, will have an overall combined weight of from 1 to 5 pounds. This weight can vary by the size and material used for the porous cup. If this weight were insufficient to establish effective hydraulic communication with the type of soil at the base of bore 16, apparatus 10a could be constructed of denser material, or configured with separately mounted weights to effectively bring the combined weight of housing 12a and its associated components up to a desired combined weight, in accordance with the invention. If the sediment at the base of the bore is not sufficiently fine to establish hydraulic communication under the weight of the apparatus alone, a small amount of silica flour may be placed in the hole prior to placing the tensiometer into contact with the bottom of the hole to enhance the contact area and hydraulic contact between the large grains and the porous cup. A goal is to provide a force contact between the cup and soil of from approximately 0.1 to 10 pounds per square inch.

Another alternate embodiment tensiometer apparatus 10b is diagrammatically shown and described with reference to FIG. 4. Again, like numbers from the FIGS. 1 and 2 embodiment are utilized where appropriate, with differences being indicated by different numerals or a suffix "b". In this embodiment, housing 12b is comprised of a lower portion 52 and an upper portion 54. Upper portion 54 and lower portion 52 are interconnected via a threaded PVC connection 56. Lower portion 52 is provided with a fluid chamber 26b which is in fluid communication with porous tip 24b. Tubing 58 extends upwardly into upper portion 54 and terminates in a rubber septum 60. Such is permeable, by example utilizing a syringe needle, for access with a pressure sensing device, and is provided in fluid communication with fluid chamber 26b through tubing 58.

To utilize such a device, de-aired water would first be injected within chamber 26b by removing septum 60 to either completely fill such chamber or provide some desired level therewithin. Septum 60 is then placed back on tubing 58, thereby pressurizing the water in chamber 26b. The apparatus is then inserted into a borehole as described with respect to the FIGS. 1–3 embodiments. After a suitable time has elapsed such that equilibrium between the device and the surrounding sediment at the base of the bore has occurred, the device would be raised above grade. There, septum access port 60 would again be accessed by some pressure sensing device to determine pressure within the chamber. Accordingly in this described embodiment, body 12b in operation is void of any mounted pressure sensing device.

Another alternate embodiment tensiometer and method to in situ determine below-grade soil moisture potential is described with reference to FIGS. 5 and 6. Like numerals from the first-described embodiments are utilized with a suffix "c" or different numerals to distinguish construction. Tensiometer apparatus 10c includes a body 12c which is adapted for insertion into a bore in earthen soil below grade. Body 12c is elongated and has surrounding lateral sidewalls 13. Body 12c is substantially hollow defining an internal fluid chamber 26c. An arcuate or curved laterally-oriented, porous material 24c is provided relative to one of body lateral sidewalls 13, and in part defines a boundary of fluid chamber 26c within body 12c. A pressure transducer 30c is provided externally of housing 12c, and communicates with chamber 26c via a conduit 59. Accordingly in the illustrated embodiment, pressure transducer 30c is mounted externally of housing or body 12c. It could of course also be directly connected to sidewalls 13, or retained internally relative to housing 26c. A fill tube 61 extends outwardly of housing 12c, and communicates with fluid chamber 26c. A sealing cap 62 is provided to seal fluid chamber 26c. An electric lead 34c would extend from transducer 30c to the surface. Component 65 diagrammatically illustrates either a flexible line or a rigid rod for utilization in raising or lowering housing 12c relative to a borehole in which the apparatus will be utilized for tensiometric measurements. Alternately, 10c can be raised and lowered using the electrical leads.

To utilize such a device, fluid chamber 26c would be filled with a degassed liquid via fill tube 61. Thereafter, body 12c would be inserted into a bore or trench below grade in earthen soil. Porous member 24c would be laterally urged against a sidewall of the earthen bore to effectively establish hydraulic communication between fluid chamber 26c and earthen material. Degassed liquid would permeate the porous material to cause a change in pressure in fluid chamber 26c, which would be monitored by pressure transducer 30c. Such a construction method provides an advantage of obtaining tensiometric measurements via sidewall bore access as opposed to hydraulic access within the bore at the base.

Figure 8:
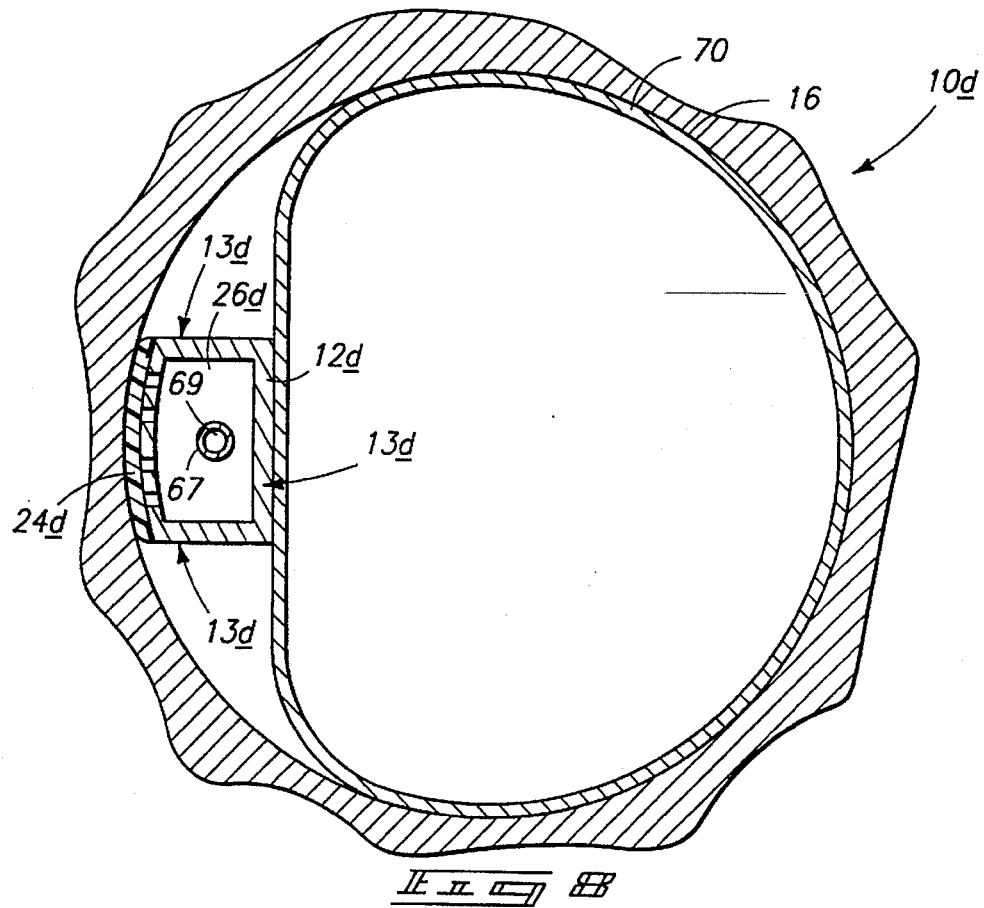
FIG. 8 is a sectional view taken through line 8—8 of FIG. 7.

FIGS. 7 and 8 illustrate a reduction-to-practice tensiometer apparatus 10d in accordance with an aspect of the invention. Again, like numerals are utilized with distinctions and construction being indicated by different numerals or a suffix "d". Body 12d is configured with a bottom opening 67 (FIG. 8) which is sealable by means of a rubber stopper 69. Such opening is utilizable to fill fluid chamber 26d with degassed fluid. Porous material 24d in one of body sidewalls 13d preferably has an arcuate periphery, as shown, corresponding in male size and shape to a female arcuate periphery size and shape of the size of bore 16 for which the apparatus is primarily adapted.

An inflatable bladder 70 is provided laterally of porous material 24d against one of lateral sidewalls 13d of housing 12d. Such is preferably adhered by an adhesive or other means to the outer portion of sidewall 13d. An inflation/deflation hose 71 extends outwardly of bladder 70 to an above-grade location.

When positioning apparatus 10d within bore 16, bladder 70 would be initially deflated and the apparatus then lowered to a desired depth within the soil. Thereafter, bladder 70 would be inflated with a fluid (either liquid or gas, or a combination thereof). Such causes the bladder to engage a portion of a sidewall of bore 16 to laterally urge porous material 26d into hydraulic communication with earthen soil of another portion of the bore sidewall, as shown. Tensiometric measurements are then determined after equilibrium is reached, as described above.

Alternate mechanisms might also be utilized for urging porous material 24d against the sidewall of a bore. FIG. 9, by way of example only, illustrates one such alternate construction 10e. Such illustrates in diagrammatic form a piston and cylinder assembly 72 which is positioned laterally of porous tip 24e for expanding the lateral expanse of the apparatus for urging porous material 24e against the sidewall of the bore.

Figure 10:
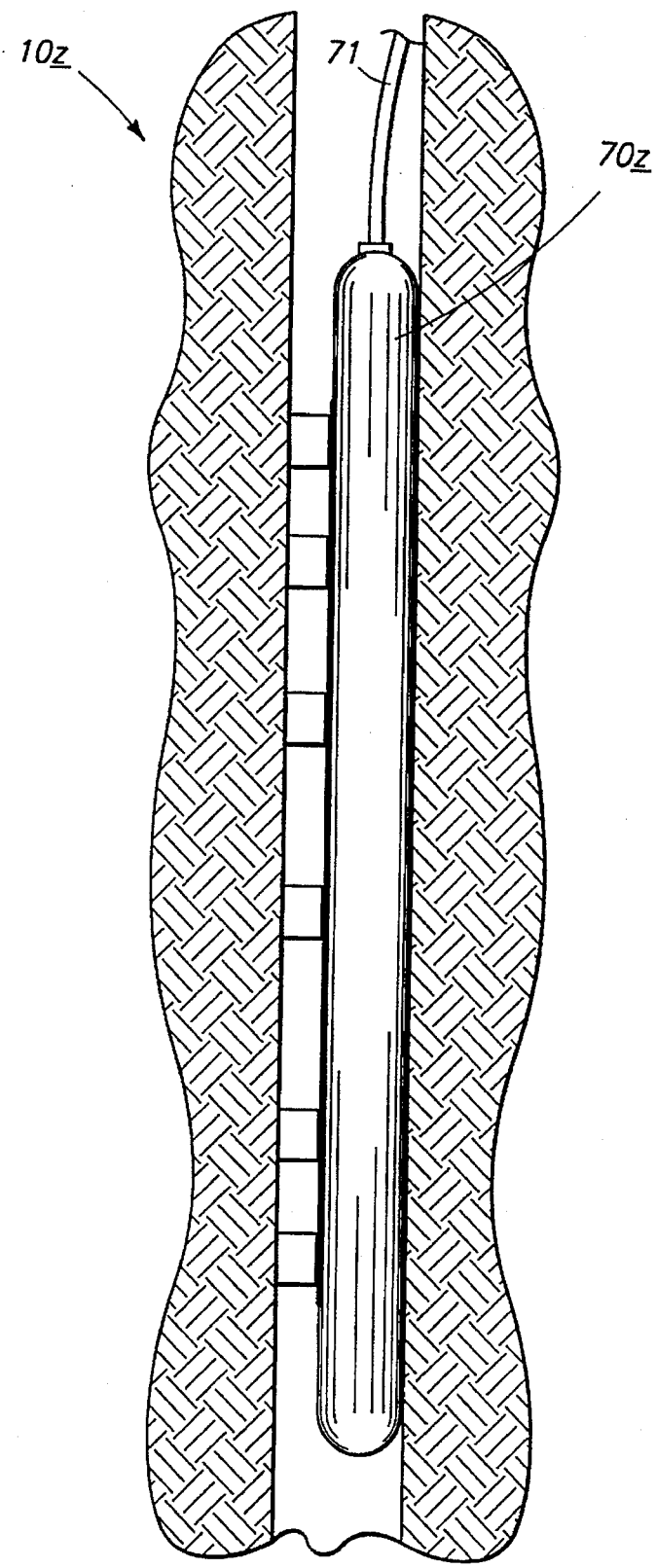
FIG. 10 is a longitudinal sectional view of another alternate embodiment sidewall tensiometer apparatus in accordance with the invention.

Another alternate embodiment 10z is diagrammatically shown in FIG. 10. Such diagrammatically comprises a plurality of sensors adhered to one side of a common inflatable bladder 70z at different elevations. This would enable moisture potential to be measured at different elevations within the soil. The sensors could be adhered to bladder 70z by velcro.

The above sidewall tensiometric measuring apparatus might of course also be constructed without an attached pressure sensing member, and instead use an accessible septum like the FIG. 4 embodiment. For example, cap 62 (FIGS. 5 and 6) could comprise a septum.

Yet another alternate embodiment tensiometer apparatus 10f is illustrated in FIGS. 11 and 12. In this embodiment, a thin porous plastic sheet 24f is combined with a non-porous acrylic or PVC backing sheet 77. An example and preferred material for sheet 24f is wettable porous plastic (A-20 or A-40) manufactured by FMC. Backing sheet 77 is configured to provide a void 78 within the device, which is completely filled with a porous material 83. An example and preferred material is a plastic or fiberglass screen, or a scrim material. Sheets 24f and 78 are adhered to one another in fluid-tight communication via perimeter adhesive 79. A passageway 80 extends from the rear of non-pervious backing 77 to void 78, which is filled with screen 83. A PVC fitting 82 having opening 80 extending therethrough is provided against backing plate 77, and communicates with a conduit 84. Conduit 84 branches to fluid communicate with a transducer 30f, and a fill conduit 86.

Suitable bore sidewall engaging means such as an inflatable bladder would also be associated with the device, as described above. Such would be inflated once the device were inserted within a borehole to urge or push material 24f outwardly against the bore sidewall. The described materials are sufficiently flexible to enable the apparatus to curve or bend to conform to the general arcuate sidewall shape to provide intimate contact with the sidewall. Thus, this embodiment provides flexible, lateral sidewalls having porous material received therein which in this embodiment substantially fills the void, and is capable of flexibly conforming to the internal sidewalls surfaces.

In compliance with the statute, the invention has been described in language more or less specific as to structural and methodical features. It is to be understood, however, that the invention is not limited to the specific features shown and described, since the means herein disclosed comprise preferred forms of putting the invention into effect. The invention is, therefore, claimed in any of its forms or modifications within the proper scope of the appended claims appropriately interpreted in accordance with the doctrine of equivalents.

We claim:

1. A portable tensiometer to in situ determine below-grade soil moisture potential of earthen soil within a bore hole comprising:

a body having opposite first and second ends and being adapted for complete insertion into earthen soil below grade;

a porous material provided at the first body end, the porous material at least in part defining a fluid chamber within the body at the first body end, the fluid chamber being fluidically sealed within the body but for the porous material;

a degassed liquid received within the fluid chamber;

a pressure transducer mounted in fluid communication with the fluid chamber and on the body;

the body, pressure transducer and degassed liquid having a combined mass of about 1 to about 5 pounds;

a suspension means connected to the body adjacent the second body end, the suspension means being of sufficient strength to gravitationally freely self suspend the combined mass and to lower said combined mass down the bore hole such that the porous material contacts the earthen soil within the bore hole; and the combined mass being sufficient to effectively impart hydraulic communication between below-grade earthen soil contacted by the porous material under the weight of the combined mass, the combined mass producing a force contact between the porous material and the soil of about 0.1 to about 10 pounds per square inch of surface area of the porous material.

2. The tensiometer of claim 1 wherein the pressure transducer is mounted externally to the body.

3. A method of monitoring soil moisture potential in below-grade earthen soil comprising the following steps:

providing a body having opposing first and second ends, a porous material provided at the first body end, the porous material at least in part defining a fluid chamber within the body at the first end, the fluid chamber being fluidically sealed within the body but for the porous material, a degassed liquid received within the fluid chamber, a pressure transducer mounted in fluid communication with the fluid chamber and on the body, the overall combined weight of the porous body, porous material, degassed fluid and pressure transducer being about 1 to about 5 pounds;

lowering the body, transducer and degassed liquid below grade into an opening provided in earthen soil using a flexible line attached to the body adjacent the second body end;

continuing to lower the body, transducer and degassed liquid within the opening until the porous material reaches and contacts a lowestmost base terminus of the earth opening;

slackening the flexible line to self support the body, transducer, and degassed liquid against the earth opening base through the porous material under their own combined weight, the weight being sufficient to establish effective hydraulic communication between the earthen soil and the porous material;

permitting the degassed liquid to permeate the porous material to cause a change in pressure in the fluid chamber; and determining the change in pressure with the pressure transducer.

4. A tensiometer for determining below-grade soil moisture potential of earthen soil within a bore hole, comprising, a body defining a fluid chamber, the entire body inserted below grade;

a porous material borne by the body and defining in part the fluid chamber;

a degassed fluid received within the fluid chamber;

a transducer substantially permanently mounted on the body and operably disposed in fluid communication with the fluid chamber, the body, porous material and degassed fluid having a given combined mass; and a suspension means mounted on the body and operable to freely self-suspend the combined mass, and to lower said combined means down said bore hole such that the porous material contacts the earthen soil within said bore hole, the combined mass producing a force contact between the porous material and the below-grade soil of about 0.1 to about 10 pounds per square inch of surface area of the porous material.

\* \* \* \* \*